United States Patent [19]

Gawryl et al.

[11] Patent Number: 5,808,011
[45] Date of Patent: Sep. 15, 1998

[54] METHOD FOR CHROMATOGRAPHIC REMOVAL OF PRIONS

[75] Inventors: Maria S. Gawryl, Charlestown; Robert A. Houtchens, Milford; William R. Light, Natick, all of Mass.

[73] Assignee: Biopure Corporation, Cambridge, Mass.

[21] Appl. No.: 673,147

[22] Filed: Jul. 1, 1996

[51] Int. Cl.$^6$ ........................................... C07K 1/18
[52] U.S. Cl. .................. 530/416; 530/414; 530/412; 530/385
[58] Field of Search ................... 530/385, 412, 530/414, 416

[56] References Cited

FOREIGN PATENT DOCUMENTS

| 0 307 373 A2 | 9/1988 | European Pat. Off. . |
| 0 313 343 | 4/1989 | European Pat. Off. . |
| 95/05846 | 2/1996 | WIPO . |

OTHER PUBLICATIONS

Bolton et al. (1985) J. Virology, 53/2, pp. 596–606. 1985.
Pergami, P. et al. (1996) Anal. Biochem. 236, 63–73. 1996.
Smith, E. et al. (1983) Principles of Biochemistry, General Aspects 7th Ed. pp. 164–167. 1983.
Walker, S. G., et al., "Aqueous two–phase partition of complex protein feedstocks derived from brain tissue homogenates," J. Chromatogr. B., 680:91–96 (1996).
Pan, K–M, et al., "Purification and properties of the cellular prion protein from Syrian hamster brain," Protein Science vol. I:1343–1352 (1992).
Pocchiari, M., et al., "Can potential hazard of Creutzfeldt–Jakob disease infectivity be reduced in the production of human Growth Hormone?", Arch Virol, 98:131–135 (1988).
DiMartino, A., "Transmissible Spongiform Encephalopathies and the Safety of Naturally–derived Biologicals," Biologicals, 21:61–66 (1993).
Walker, A.S., et al., "Conditions for the Chemical and Physical Inactivation of the K. Fu. Strain of the Agent of Creutzfeldt–Jakob Disease," AJPH, 73(6) :661–665 (Jun. 1983).
Prusiner, S. B., "Molecular Biology of Prion Disease", Science 252: 1515–1522 (Jun. 1991).

Brown, P., et al., "Concise Communications, Newer Data on the Inactivation of Scrapie Virus or Creutzfeldt–Jakob Disease Virus in Brian Tissue", J. of Infectious Diseases 153 (6):1145–1148 (Jun. 1986).
Prusiner, S. B., et al., "Thiocyanate and hydroxyl ions inactivate the scrapie agent", Proc. Natl. Acad. Sci., USA 78(7) :4606–4610 (Jul. 1981).
Brown, P., et al., "Potential Epidemic of Creutzfeldt–Jakob Disease from Human Growth Hormone Therapy", The New England J. of Medicine, 313(12) : 782–731 (Sep. 1985).
Cheseboro, B., "Spongiform Encephalopathies: The Transmissible Agents", Virology, 2nd edition, edited by B.N. Fields, D.M. Kinpe et al., Raven Press, Ltd., NY pp. 2325–2336 (1990).
Millson G.C. and Manning, E. J., "Effect of Selected Detergents on Scrapie Infectivity", in *Slow Transmissible Diseases of the Nervous System* Academic Press, eds. Stanley B. Prusiner and William J. Hadlow (vol. 2), pp. 409–424 (1979).
Kimberlin, R. H., et al., "Disinfection Studies with Two Strains of Mouse–Passaged Scrapie Agent", J. Neurol. Sci. 59: 355–369 (1983).
Department of Health and Social Security (DHSS), "Advisory Group on the Management of patients with Spongiform Encephalopathy (Creutzfeldt–Jakob Disease (CJD)", Report to the Chief Medical Officers of the Heath Departments of Great Britain, pp. 1–5.(1984).

*Primary Examiner*—Robert A. Wax
*Assistant Examiner*—Enrique D. Longton
*Attorney, Agent, or Firm*—Hamilton, Brook, Smith & Reynolds, P.C.

[57] ABSTRACT

A method for removing a prion from a solution comprising the prion and at least one additional biomolecule, comprising directing the solution through an anion-exchange chromatography column under conditions that cause a gradient elution, whereby the prion is separated from at least one of the biomolecules, thereby causing said biomolecule to be collected in an eluate fraction that is distinct from an eluate fraction that includes the prion. In one embodiment, the gradient is a pH gradient, for example, a step gradient. The prion can be a causal agent for a spongiform encephalopathy, such as Creutzfeldt-Jakob disease, Gerstmann-Straussler-Scheinken syndrome, scrapie, or bovine spongiform encephalopathy.

19 Claims, No Drawings

METHOD FOR CHROMATOGRAPHIC REMOVAL OF PRIONS

BACKGROUND OF THE INVENTION

Spongiform encephalopathies are mammalian diseases of the central nervous system that result in presenile dementia and are typically fatal. Among these are the human diseases Creutzfeldt-Jakob disease, kuru and Gerstmann-Straussler-Scheinken syndrome, the ovine disease scrapie, and bovine spongiform encephalopathy. Although there is strong evidence that these diseases are caused by a common agent or a set of closely related agents, the nature of these agents is at present poorly defined (Prusiner, *Science* 252 : 1515–1522 (1991)). A growing body of evidence suggests that a protease resistant posttranslationally modified form of a host cellular protein plays a causal role, but it is not known if this altered protein alone is the causal agent or if it is a necessary component of the causal agent. This protein has been denoted prion protein (hereinafter referred to as "PrP") and the infectious agents of the spongiform encephalopathies are referred to as prions.

Although they are not generally infectious, there is evidence that under certain conditions at least some spongiform encephalopathies can be passed from one animal to another, and in certain cases, can cross from one species to another. For example, in the 1970's a series of cases of Creutzfeldt-Jakob disease were reported in individuals that had undergone treatment with human growth hormone purified from pooled pituitary glands (Brown et al., *N. Eng. J. Med.* 313:728–731 (1985)). It is believed that the first appearance of bovine spongiform encephalopathy resulted from transmission of ovine scrapie to cattle via contaminated feed. Also, a murine model for scrapie have been developed by intracranial injection of contaminated ovine tissue into mice.

The determination of prions in tissue or other biological products currently relies upon assays measuring infection of mice or hamsters with extracts of the biological material in question. As the incubation period for these diseases can be a year or longer, such studies are lengthy and expensive to perform.

The widespread occurrence of prion-related disease and the possibility of interspecies transmission has serious implications for the biotechnology industry, which derives many of its products from mammalian tissue (Di Martino, *Biologicals* 21 : 61–66 (1993)). Concerns about the safety of such products has led to studies on the inactivation of prions. These studies indicate that prions are more resistant toward inactivation than more conventional pathogens such as viruses or bacteria. Thus, relatively harsh conditions are required to decontaminate prion-containing biological materials. The only methods currently known to disinfect high prion titer biological preparations are prolonged autoclaving at 130° C. or above and treatment with concentrated sodium hydroxide solution. These methods have been recommended for routine inactivation of prions *(Department of Health and Social Security Circular* 84 : 16 (1989)). It has also been reported that 100 kD cutoff ultrafiltration in combination with treatment with 6M urea results in decontamination of prion containing preparations (Pocchiari et al., Arch. *Virol.* 98 : 131–135 (1988)). Other methods capable of lowering prion activity include treatment with organic solvents, detergents, protein-denaturing agents, chaotropic salts and phenol (Millson et al., in Prusiner and Hadlow, eds. Slow Transmissible Diseases of the Nervous System, vol. II. New York: Academic Press 409–424 (1979); Prusiner et al., PNAS 78 : 4606–4610 (1981); Kimberlin et al., *J. Neurol. Sci.* 59 : 390–392 (1983); Walker et al., Am. *J. Public Health* 73 : 661–665 (1983); Brown et al., *J. Infect. Dis.* 153 : 1145–1148 (1986)).

The extreme conditions required to eliminate prion infectivity are typically incompatible with methods intended to preserve biomolecules having useful activity, resulting in the denaturation of many biomolecules and thereby essentially destroying their activity. There is, thus, a need for a method for removing prions from biological materials or inactivating prions under conditions that do not compromise the activity of desirable biomolecules.

SUMMARY OF THE INVENTION

The present invention relates to a method for removing a prion from a solution that includes the prion and at least one additional biomolecule.

The method includes the step of directing the solution through an anion-exchange chromatography column under conditions that cause a gradient elution, whereby the prion is separated from at least one of the biomolecules, thereby causing said biomolecule to be collected in an eluate fraction that is distinct from an eluate fraction that includes the prion.

In another embodiment, the present invention provides a method for removing a prion from a solution which includes the prion and hemoglobin. The method comprises the step of directing the solution through an anion exchange chromatography column under conditions that cause a gradient elution. This separates the prion from the hemoglobin, with the prion eluting in a fraction which is distinct from the fraction which includes the hemoglobin.

The method of the invention can be performed under mild conditions, without the use of heat, strong alkali or oxidizing agents. Thus, the present invention enables the decontamination of solutions that include prions in the presence of a variety of other biomolecules, without significantly affecting the activity of the other biomolecules.

DETAILED DESCRIPTION OF THE INVENTION

The features and other details of the method of the invention will now be more particularly described and pointed out in the claims. It will be understood that the particular embodiments of the invention are shown by way of illustration and not as limitations of the invention. The principle features of the invention can be employed in various embodiments without departing from the scope of the present invention.

The present invention is based upon the discovery that chromatographing a prion-spiked bovine hemoglobin solution on an anion exchange column eliminates a surprisingly high level of prion infectivity from the eluted hemoglobin fraction. The method of the present invention for removing a prion from a solution comprising a prion and at least one other biomolecule comprises directing the solution through an anion exchange chromatography column under conditions that cause a pH gradient elution. The prion is thus separated from at least one of the biomolecules, that is, at least one of the biomolecules elutes off of the column in a fraction that is distinct from the fraction which includes the prion.

For the purposes of the present invention, the term "prion" refers to a protein which is a causal agent of a central nervous system disease. The term "causal agent" is intended to refer to an agent which either causes the disease in question or is a necessary component of a disease-producing system. Prion-associated diseases include the various spongiform encephalopathies, such as the human diseases Creutzfeldt-Jakob disease, kuru, and Gerstmann-Straussler-Scheinken syndrome, the ovine disease scrapie, bovine spongiform encephalopathy and transmissible mink encephalopathy. The prion can be, for example, a protein, such as a posttranslationally modified PrP protein, or it can be a protein complexed with an informational molecule, such as a polynucleotide, for example, a polydeoxyribonucleotide complexed with a posttranslationally modified PrP protein.

For the purposes of the present invention, the term "biomolecule" refers to any molecule of biological origin, including proteins, such as enzymes, antibodies, structural proteins and transport proteins, polypeptides, hormones, such as growth hormones, insulin and steroid hormones, polynucleotides, sugars and lipids. For the purposes of the present invention, preferred biomolecules are proteins, polypeptides and polynucleotides having realized or potential utility.

Suitable pH gradients which can be employed for eluting the anion exchange chromatography column include, for example, a continuous pH gradient, wherein the pH of the eluent is changed continuously as a function of time. An example of a continuous pH gradient is a linear pH gradient, wherein the change in pH is a linear function of time. A continuous pH gradient can be established by utilizing two or more buffers of differing pH which are mixed together to form the eluent. The ratio of the buffers within the eluent, and, thus, the pH of the eluent, can thus be varied continuously as a function of time. Control of the buffer mixing process is typically controlled by a flow controller, which is programmed to produce the desired pH gradient.

In another embodiment, the pH gradient can be a step pH gradient, wherein the change in pH is discontinuous with respect to time, forming one or more steps, or time points wherein the pH undergoes an abrupt change. This can be accomplished simply by replacing as eluent a first buffer with a second buffer of different pH. In a preferred embodiment of the method the gradient employed is a step pH gradient.

In one method for performing a step pH gradient elution, each of a series of buffers having different pH values is sequentially directed into the chromatographic column. It is preferred that the buffers are filtered, such as through a 10,000 Dalton depyrogenation membrane. The buffers used should be monovalent buffers with a low ionic strength, so that elution of the solution components is generally dependent upon pH and not significantly dependent upon ionic strength. Typically, buffers with an ionic strength of about 50 mM or less have a suitably low ionic strength.

Examples of anion exchange media which are suitable for the present method include silica, alumina, titania, cross-linked dextran, agarose, or a derivatized polymer or copolymer, such as a polyacrylamide, a polyhydroxyethyl-methacrylate or a styrene divinylbenzene, that has been derivatized with a cationic functionality, such as a diethylaminoethyl or quaternary aminoethyl group.

In a preferred embodiment, the anion exchange medium is based on silica gel. This medium is formed by hydrothermally treating silica gel to increase pore size, and then exposing the gel to (γ-glycidoxy-propyl)trimethoxysilane to form active surface epoxide groups. The derivatized silica is then treated with a tertiary amine, such as $HOCH_2CH_2N(CH_3)_2$, to form surface quaternary ammonium groups.

The anion exchange chromatography column can be, for example, a gravity column, i.e., a column through which the mobile phase flows under the force of gravity. The mobile phase can also be subjected to a pressure difference between the column inlet and outlet, such as by directing a pressurized fluid into the column inlet subsequent to loading the sample onto the column. In a preferred embodiment, the anion exchange chromatography column is a high performance liquid chromatography column.

In one embodiment, the solution comprises a prion and hemoglobin, such as bovine hemoglobin. In this embodiment, the first buffer transports the solution into the medium in the chromatographic column and facilitates binding of the hemoglobin to the medium. The second buffer then adjusts the pH within the medium to elute non-hemoglobin components, such as the prion. The third buffer then elutes hemoglobin which is substantially free of the prion. The first and last portions of the hemoglobin-containing eluent, for example the first 3% to 4% and the last 3% to 4%, can be discarded to provide assurance of the purity of the hemoglobin.

Preferably, the first buffer is a tris-hydroxymethyl aminomethane (Tris) solution (concentration about 20 mM, having a pH in the range of between about 8.4 and about 9.4). The second buffer is a mixture of the first buffer and a third buffer, with the second buffer having a pH in the range from about 8.2 to about 8.6. The third buffer is a Tris solution (concentration about 50 mM, having a pH in the range of between about 6.5 and about 7.5). The fourth buffer is a NaCl/Tris solution (concentrations about 1.0M NaCl and about 20 mM Tris; having a pH in the range of about 8.4 and about 9.4, preferably from about 8.9 to about 9.1). It is particularly preferred that the pH of the second buffer be between about 8.2 and 8.4.

The buffers employed are typically at a temperature in the range from about 0° C. to about 50° C. Preferably, buffer temperature is about 12.4°±1.0° C. during use. In addition, the buffers are typically stored at a temperature of about 9° C. to about 11° C.

In another embodiment, the method further comprises directing the solution through an ultrafiltration membrane. This step can be performed before or after the anion exchange chromatography step. In a preferred embodiment, the solution is directed under pressure through the ultrafiltration membrane, such as a 100,000 Dalton membrane, prior to anion exchange chromatography. Examples of ultrafiltration membranes which are suitable for this method include 100,000 Dalton membranes available from Millipore Corporation (Bedford, Mass., catalog no. CDUF 050 H1) and A/G Technology (Needham, Mass., model no. UFP100E55).

In one embodiment, the solution comprises a prion which is a causal agent for bovine spongiform encephalopathy and a second bovine protein. The second bovine protein can be, for example, bovine hemoglobin, bovine growth hormone, bovine immunoglobulin, bovine insulin, bovine serum albumin, bovine aprotinin, bovine transferrin, bovine serum, bovine thrombin or bovine fibrinogen. In a preferred embodiment, the second bovine protein is bovine hemoglobin.

In another embodiment, the solution comprises a prion which is a causal agent for a spongiform encephalopathy, such as scrapie, Creutzfeldt-Jakob disease, kuru, Gerstmann-Straussler-Scheinken disease and one or more additional biomolecules derived from human or other mammalian tissue, such as a protein or a hormone. Examples of suitable additional biomolecules include hemoglobin, insulin, growth hormone, gonadotropin, myelin, collagen, elastin, serum, serum albumin, lactalbumin, antibodies and antisera, Factor VIII, Factor IX, prothrombin and thrombin, erythropoetin, tissue plasminogen activator, platelet activating factor, proteases, protease inhibitors, interferons, interleukins, and cytokines.

The invention will now be further and specifically described in the following examples.

EXEMPLIFICATION

EXAMPLE 1

Purification of bovine hemoglobin solution by anion exchange chromatography Preparation of bovine hemoglobin solutions A bovine hemoglobin solution was prepared according to the method described in U.S. patent application No. 08/473, 497. Samples of whole bovine blood were collected, mixed with a sodium citrate anticoagulant to form a citrated blood solution, and then analyzed for endotoxin levels. The blood solution samples were maintained after collection at a temperature of about 2° C. and then strained to remove large aggregates and particles with a 600 mesh screen.

The citrated blood solution was then passed in series, through 800 $\mu$m and 50 $\mu$m polypropylene filters to remove large blood solution debris.

The red blood cells were then washed to separate extracellular plasma proteins, such as BSA or IgG, from the red blood cells. To wash the red blood cells, the blood solution was placed in a diafiltration tank and then diluted with an equal volume of an isotonic solution that had been filtered through a 10 kD ultrafiltration membrane (commercially available from Millipore Corporation, cat. no. CDUF 050 G1). The isotonic solution was composed of 6.0 g/L sodium citrate dihydrate and 8.0 g/L sodium chloride in water-for-injection (WFI).

The diluted blood solution was then concentrated back to its original volume by diafiltration through a 0.2 $\mu$m hollow fiber (Microgon Krosflo II microfiltration cartridge, Spectrum/Microgon, Laguna Hills, Calif.) diafilter. Concurrently, filtered isotonic solution was added continuously, as makeup, at a rate equal to the rate of filtrate loss through the diafilter. During diafiltration, blood components significantly smaller than red blood cells or in solution, such as plasma solutes, passed through the walls of the diafilter with the filtrate. Red blood cells, platelets and larger bodies of the diluted blood solution, such as white blood cells, were retained with continuously added isotonic solution to form a dialyzed blood solution.

During red blood cell washing, the diluted blood solution was maintained at a temperature of between approximately 10° C. to 25° C. with a fluid pressure at the inlet of the diafilter between about 25 psi and about 30 psi to improve process efficiency.

Red blood cell washing was complete when the volume of diafiltrate equalled about 600% of the volume of blood solution prior to diluting with the isotonic solution.

The dialyzed blood solution was then continuously pumped at a rate of approximately 4 liters per minute to a Sharples Super Centrifuge (Model No. AS-16, Sharples Division of Alfa-Laval Separation, Inc.), fitted with a no. 28 ringdam. The centrifuge was operating while concurrently being fed dialyzed blood solution, to separate the red blood cells from the white blood cells and platelets. During operation, the centrifuge rotated at a rate sufficient to separate the blood into a heavy red blood cell phase and a light white blood cell phase, typically about 15,000 rpm. Fractions of the red blood cell phase and the white blood cell phase were separately and continuously discharged from the centrifuge during operation.

Following separation, the red blood cells were lysed to form a hemoglobin-containing solution. A substantial portion of the red blood cells were mechanically lysed upon discharge from the centrifuge, due to the impact of the cells on the wall of the red blood cell phase discharge line at an angle to the flow of the red blood cell phase out of the centrifuge, thereby releasing hemoglobin from the red blood cells into the red blood cell phase.

The lysed red blood cell phase then flowed through the red blood cell phase discharge line into a static mixer (Kenics ½ inch with 6 elements, Chemineer, Inc.). Concurrent with the transfer of the red blood cell phase to the static mixer, an equal volume of WFI was also injected into the static mixer, wherein the WFI mixed with the red blood cell phase. The flow rates of the red blood cell phase and the WFI into the static mixer are each at about 0.25 liter per minute.

Mixing the red blood cell phase with WFI in the static mixer produced a lysed red blood cell colloid. This was then transferred to a Sharples Super Centrifuge (Model No. AS-16), which was suitable to separate the hemoglobin from the non-hemoglobin red blood cell components. The centrifuge was rotated at a rate sufficient to separate the lysed red blood cell colloid into a light hemoglobin phase and a heavy phase. The light phase was composed of hemoglobin and also contained non-hemoglobin components with a density approximately equal to or less than the density of hemoglobin.

The hemoglobin phase was continuously discharged from the centrifuge, through a 0.45 $\mu$m Pellicon Cassette microfilter (Millipore Corporation, cat. no. HVLP 000 C5), and into a holding tank in preparation for hemoglobin purification. Cell stroma were then returned with the retentate from the microfilter to the holding tank. During microfiltration, the temperature of the holding tank was maintained at 10° C. or less. To improve efficiency, when the fluid pressure at the microfilter inlet increased from an initial pressure of about 10 psi to about 25 psi, microfiltration was complete. The hemoglobin microfiltrate was transferred from the microfilter to the microfiltration tank. The microfiltrate was at this stage divided into two samples, Samples A and B. Sample A was not further purified at this point.

Sample B was subsequently pumped through a 100 kD ultrafilter (Millipore Corporation, cat. no. CDUF 050 H1). A substantial portion of the hemoglobin and water, contained in the microfiltrate, permeated the ultrafilter to form a hemoglobin ultrafiltrate, while larger microfiltrate components, such as proteins of molecular weight greater than about 100 kD, were retained and recirculated back to the microfiltration tank. Concurrently, WFI was continuously added to the microfiltrate tank as makeup for water lost in the ultrafiltrate. Ultrafiltration continued until the concentration of hemoglobin in the microfiltrate tank was less than 8 grams/liter. During the ultrafiltration step, the internal temperature of the microfiltrate tank was maintained at about 10° C.

The hemoglobin ultrafiltrate was then transferred to an ultrafiltration tank, and recirculated through a 30 kD ultrafilter (Millipore Corporation, cat. no. CDUF 050 T1) to remove smaller cell components, such as electrolytes, metabolic intermediates, water and proteins of molecular weight less than about 30 kD. This resulted in a concentrated hemoglobin solution containing about 100 grams per liter hemoglobin. Initial purification of Sample B was concluded at this point. Preparation of anion exchange chromatographic medium Silica gel was treated with (γ-glycidoxy-propyl) trimethoxysilane in water at 70° C., yielding a silica derivatized with surface epoxide groups. This derivatized silica gel was then treated with N,N-dimethylethanolamine ($OHCH_2CH_2)N(CH_3)_2$ yielding a silica gel derivatized with surface quaternary ammonium groups. Spiking of samples with scrapie agent The scrapie agent used in the studies described herein was the murine-adapted ME-7 strain licensed from the Institute of Animal Health, Edinburgh, Scotland. The original source of the agent was a natural scrapie infection of Suffolk sheep. Brain extract from these sheep underwent two passages through Moredun random bred mice, nine passages through C57BL/6N, one passage through $C_3H$ mice and one additional passage through C57BL/6N mice. The spiking material used in this study was at passage level thirteen.

Sample A (180 mL) was spiked with a 20 mL volume of the scrapie agent to yield Sample A'. An aliquot of Sample A' was retained for use in "prove spike" assays, and the remainder was subjected to ultrafiltration through a 100 kD ultrafilter, as described above for Sample B. The resulting ultrafiltrate, now designated Sample A", was assayed for scrapie infectivity as described in Example 2.

A 20 mL aliquot of Sample B was spiked with 2 mL of scrapie agent to yield Sample B'. An aliquot of Sample B' was retained for use in control "prove spike" assays. The remainder of the spiked sample was subjected to anion exchange chromatography. The spiked Sample B' was directed onto the media contained in a chromatography column, to purify the hemoglobin by anion exchange high performance liquid chromatography. The column had an 8 inch inner diameter and a length of 24 inches. The anion exchange medium within the column was the silica-based medium described above.

The column was pretreated with a buffer which facilitates hemoglobin binding to the medium. Then the Sample B' was injected into the column at a flow rate of 1.78 liters per minute. The column was then washed by successively directing three different buffers through the column to produce a hemoglobin eluate, by producing a pH gradient within the column. The temperature of each buffer during use was about 12.4° C. The buffers were prefiltered through a 10 kD ultrafiltration membrane (Millipore Corporation, cat. no. CDUF 050 G1) before injection onto the column. The flow rate of each buffer through the column was 3.56 liters per minute.

The first buffer, 20 mM tris-hydroxymethylaminomethane (Tris, pH in the range from about 8.4 to about 9.4), transported the concentrated hemoglobin solution into the anion exchange medium within the column. The second buffer, a mixture of the first buffer with a third buffer and having a pH of about 8.3, then adjusted the pH within the column to elute contaminating components while retaining the hemoglobin. Equilibration with the second buffer continued for about 30 minutes. The eluent from the second buffer was discarded to waste. The third buffer, 50 mM Tris (pH in the range from about 6.5 to about 7.5), then eluted the hemoglobin from the column. The first and last 3% to 4% of the hemoglobin eluent was discarded. The remaining hemoglobin eluent, now designated Sample B", was assayed for scrapie infectivity as described in Example 2.

EXAMPLE 2
Validation of prion removal method in bovine hemoglobin preparation

Method validation was performed at a registered facility, following procedures in compliance with the U.S. Food and Drug Administration Good Laboratory practice Regulations (21 CFR 58), the United Kingdom GLP Compliance Programme, the Japanese GLP Standard and the OECD Principles of Good Laboratory Practice.

The solutions evaluated via the in vivo assay for scrapie infectivity were 1. the scrapie agent solution used to spike the hemoglobin solutions, 2. Sample A', 3. Sample A", 4. Sample B' and 5. Sample B". In vivo assay The in vivo assay for scrapie infectivity was performed by Microbiological Associates, Rockville, Md., according to a published method (Chesebro, Spongiform Encephalopathies: the Transmissible Agents, in *Virology*, Fields, Knipe, et al., eds. Raven Press LTD.: New York, Chapter 81, pp. 2325–2336 (1990)). The method involves intracranial inoculation of mice with an aliquot of a solution of interest, monitoring the mice for clinical signs of scrapie infection and determining survival rates over the course of one year.

Scrapie infectivity was assayed for the following solutions: the spiking material, Sample A' (clarified and unclarified), Sample A", Sample B', and Sample B". A series of dilutions of each of these solutions was prepared as indicated: spiking material, dilution factors 1 (undilute) $10^{-3}$, $10^{-4}$, $10^{-5}$, $10^{-6}$, $10^{-7}$, and $10^{-8}$; Sample A', unclarified: dilution factor 1, clarified: dilution factors 1, $10^{-1}$; Sample A", dilution factors 1, $10^{-1}$, $10^{-2}$, $10^{-3}$, $10^{-4}$, and $10^{-5}$; Sample B', dilution factors 1 and $10^{-1}$; Sample B", dilution factors 1, $10^{-1}$, $10^{-2}$, $10^{-3}$, $10^{-4}$, and $10^{-5}$.

Female C57BL/6 mice were divided into sets of either 10 or 15 mice. A set of fifteen control mice were not inoculated, while a set of fifteen vehicle control mice were each inoculated with 0.020 mL vehicle only. The mice in each of the remaining sets were each inoculated with a 0.02 mL aliquot of a single dilution of one of the solutions under study.

The mice were monitored for clinical signs of scrapie infection for 365 days. Signs of the terminal disease stage of scrapie include sensitivity to loud noise, urinary incontinence, rough haircoat, abnormality of gait and dullness of eyes. Scrapie infection was confirmed by histopathological examination of the brain tissue of dead or sacrificed mice, wherein the presence of vacuoles in brain tissue supported a diagnosis of scrapie. Results The overall purification method for bovine hemoglobin is disclosed in U.S. patent application No. 08/473,479, the contents of which are incorporated by reference herein in their entirety. Two bovine hemoglobin solutions were prepared according to a portion of this procedure, as described in Example 1, but in each case the purification was stopped at a different point in the overall process. Sample A was purified through the microfiltration (0.45 μm pore size) step, while Sample B was purified through the diafiltration step (100 kD nominal molecular weight cut-off).

The validation procedure examined the effect of the 100 kD ultrafiltration step and the anion exchange chromatography step on the infectivity of samples spiked with the murine-adapted ME-7 scrapie agent present in the brain homogenates of infected mice. The scrapie agent was used as a model for the causal agent of bovine spongiform encephalopathy. The method employed was an in vivo assay in mice, currently the only type of assay available for prion infectivity. The infectivity of the two spiked samples prior to the purification step of interest was assayed as a control, and in both cases resulted in 100% mortality of the control mice within 365 days, with a significant majority of the mice displaying changes in brain morphology consistent with scrapie infection. In contrast spiked samples subsequently subjected to purification via 100 kD ultrafiltration or anion exchange chromatography showed no signs of scrapie infectivity in the in vivo assay.

The results of the in vivo assay are summarized in the Table, which indicates, for each test group of mice, the number of mice which survived the 365 day study, the number of mice which displayed clinical signs of scrapie during the study, the number which died or were sacrificed during the study and the number of dead mice with histopathologically confirmed scrapie.

The data show that 19 of 20 mice inoculated with spiking material at a dilution factor of $10^{-4}$ or greater displayed clinical signs of scrapie, with scrapie confirmed by histopathology. A probable inoculation error accounts for the single surviving mouse in this group.

All mice treated with unclarified, undiluted Sample A' died, but without showing signs of scrapie. The deaths are attributable to the toxic effect of solid material within this heterogeneous mixture. Each of the ten mice treated with clarified Sample A' died after displaying clinical signs of scrapie, in nine of these, scrapie was confirmed by histopathology. In one mouse in this group, substantial autolysis prevented histopathological confirmation of scrapie. In contrast, of 90 mice inoculated with a dilution of Sample A", 86 survived the study, none displayed clinical signs of scrapie, and the brains of the 4 mice that died showed normal histopathology.

Of the 5 mice inoculated with Sample B', none survived the study, and 4 of these showed both clinical and histopathological signs of scrapie. A dilution of Sample B" was administered to 90 mice. Of these, 84 survived the study, with none of the dead mice displaying clinical or histopathological signs of scrapie.

The results clearly indicate that hemoglobin solutions spiked with scrapie agent can be decontaminated under mild conditions. Purification via 100 kD ultrafiltration or anion exchange chromatography with a pH gradient elution reduced scrapie infectivity in the resulting solutions below the detection limits of the in vivo assay.

TABLE

Results of scrapie agent removal validation study.

| Sample | Dilution | Surviving/ Inoculated | No. with Clinical Signs/ No. Dead or Sacrificed | No. with Scrapie Consistent Pathology/ No. Evaluated |
|---|---|---|---|---|
| spiking material | $10^{-8}$ | 9/10 | 0/1 | 0/1 |
| spiking material | $10^{-7}$ | 9/10 | 0/1 | 0/1 |
| spiking material | $10^{-6}$ | 9/10 | 1/1 | 1/1 |
| spiking material | $10^{-5}$ | 8/10 | 2/2 | 2/2 |
| spiking material | $10^{-4}$ | 0/10 | 10/10 | 10/10 |
| spiking material | $10^{-3}$ | 1/10 | 9/9 | 9/9 |
| control | None | 12/15 | 0/3 | 0/3 |
| vehicle control | None | 15/15 | 0/0 | 0/0 |
| A' | Undilute | 0/5 | 1/5 | 1/1 |
| A' | Clarified Undilute | 0/5 | 5/5 | 5/5 |
| A' | Clarified 1:10 | 0/5 | 5/5 | 4/5 |
| A" | $10^{-5}$ | 14/15 | 0/1 | 0/1 |
| A" | $10^{-4}$ | 14/15 | 0/1 | 0/1 |
| A" | $10^{-3}$ | 14/15 | 0/1 | 0/1 |
| A" | $10^{-2}$ | 14/15 | 0/1 | 0/1 |
| A" | $10^{-1}$ | 15/15 | 0/0 | 0/0 |
| A" | Undilute | 15/15 | 0/0 | 0/0 |
| B' | Undilute | 0/5 | 4/5 | 4/5 |
| B" | $10^{-5}$ | 13/15 | 0/2 | 0/2 |
| B" | $10^{-4}$ | 13/15 | 0/2 | 0/2 |
| B" | $10^{-3}$ | 15/15 | 0/0 | 0/0 |
| B" | $10^{-2}$ | 14/15 | 0/1 | 0/1 |
| B" | $10^{-1}$ | 14/15 | 0/1 | 0/1 |
| B" | Undilute | 15/15 | 0/0 | 0/0 |

Equivalents

Those skilled in the art will recognize or be able to ascertain using no more than routine experimentation many equivalents to the specific embodiments of the invention described herein. Such equivalents are intended to be encompassed in the scope of the following claims.

We claim:

1. A method of removing a prion from a solution comprising the prion and an additional protein, comprising the step of directing the solution through an anion exchange chromatography column under conditions that cause a pH gradient elution, whereby said protein is collected in an eluate fraction which elutes from the anion exchange chromatography column at a pH between about 6.5 and about 8.3, thereby separating the prion from the collected protein.

2. The method of claim 1 wherein the pH gradient is a continuous gradient.

3. The method of claim 1 wherein the pH gradient is a step gradient.

4. The method of claim 1 wherein the anion exchange chromatography medium comprises at least one component selected from the group consisting of silica, alumina, titania, cross-linked dextran, agarose, or a polymer derivatized with cationic groups.

5. The method of claim 4 wherein the polymer is a polyacrylamide, a poly(hydroxyethylmethacrylate), or a poly(styrene-co-divinylbenzene).

6. The method of claim 4 wherein the cationic group is a quaternary ammonium group.

7. The method of claim 1 further comprising the step of filtering the solution through an ultrafiltration membrane.

8. The method of claim 7 wherein the ultrafiltration membrane has a molecular weight cutoff of about 100 Kd.

9. The method of claim 1 wherein the protein is derived from a mammal.

10. The method of claim 9 wherein the mammal is a human, or a bovine, porcine, ovine, or murine animal.

11. The method of claim 10 wherein the protein is hemoglobin.

12. The method of claim 10 wherein the prion is a causal agent for a spongiform encephalopathy.

13. The method of claim 12 wherein the spongiform encephalopathy is scrapie, Creutzfeldt-Jakob disease, kuru, Gerstmann-Straussler-Scheinken syndrome or bovine spongiform encephalopathy.

14. A method for removing a prion from a solution comprising the prion and hemoglobin, comprising the step of directing the solution through an anion exchange chromatography column under conditions that cause a gradient elution, whereby said hemoglobin is collected in an eluate fraction which elutes from the anion exchange chromatography column at a pH between about 6.5 and about 8.3, thereby separating the prion from the collected hemoglobin.

15. The method of claim 14 wherein the hemoglobin is bovine hemoglobin.

16. The method of claim 15 wherein the prion is a causal agent for bovine spongiform encephalopathy.

17. The method of claim 14 wherein the anion exchange chromatography medium comprises silica.

18. The method of claim 17 wherein the silica is functionalized with cationic groups.

19. The method of claim 18 wherein the cationic group is a quaternary ammonium group.

* * * * *